United States Patent [19]
Hairston et al.

[11] Patent Number: 5,561,515
[45] Date of Patent: Oct. 1, 1996

[54] APPARATUS FOR MEASURING PARTICLE SIZES AND VELOCITIES

[75] Inventors: Peter P. Hairston, St. Paul; Frank D. Dorman, Golden Valley; Gilmore J. Sem, Lauderdale; Jugal K. Agarwal, New Brighton, all of Minn.

[73] Assignee: TSI Incorporated, St. Paul, Minn.

[21] Appl. No.: 319,660

[22] Filed: Oct. 7, 1994

[51] Int. Cl.$^6$ .............................. G01P 5/18; G01P 5/00; G01N 21/00

[52] U.S. Cl. ........................... 356/28; 356/336; 356/342; 356/338

[58] Field of Search ............................ 356/28, 335, 336, 356/338, 28, 342

[56] References Cited

U.S. PATENT DOCUMENTS

| | | |
|---|---|---|
| 3,854,321 | 10/1974 | Dahneke . |
| 4,251,733 | 2/1982 | Hirleman, Jr. . |
| 5,037,202 | 8/1991 | Batchelder et al. . |
| 5,061,070 | 10/1991 | Batchelder et al. . |
| 5,133,602 | 7/1992 | Batchelder et al. . |

OTHER PUBLICATIONS

Article entitled "Real–Time Aerodynamic Particle Size Measurement with a Laser Velocimeter" by Jugal K. Agarwal and Leroy M. Fingerson, TSI Quarterly, Vo. V, Issue 1, Feb./Mar. 1979.

Article entitled "Four Spot Laser Anemometer and Optical Access Techniques for Turbine Applications" by Mark P. Wernet, Natl. Aeronautics & Space Admin., ICIASF 1987 Record, pp. 245–254.

Primary Examiner—Thomas H. Tarcza
Assistant Examiner—Pinchus M. Laufer
Attorney, Agent, or Firm—Frederick W. Niebuhr, Esq.

[57] ABSTRACT

An aerodynamic particle size measuring device includes a laser energy source and beam splitting, shaping and polarizing optics for forming two parallel, peripherally overlapping beams. The beams are caused to intersect a gas stream perpendicular to the direction of gas flow, thus to form a measuring volume at the intersection of the beams and flow. Single particles are carried through the measuring volume with the gas flow, each particle scattering and extinguishing light according to the beam profile, as predetermined by the degree of beam overlap and the Gaussian intensity distribution of each beam. A photodetector, responsive either to scattered light or light extinction, generates a time-dependent voltage profile that tends to replicate the intensity profile. The resulting electrical signal is processed to determine an amplitude, set a threshold for minimally acceptable amplitudes, and to derive two negative-going zero crossings for an unambiguous time/velocity determination. Logic circuitry employs the threshold in combination with the zero crossings to reject velocity readings based on single trigger or coincidence events.

40 Claims, 10 Drawing Sheets

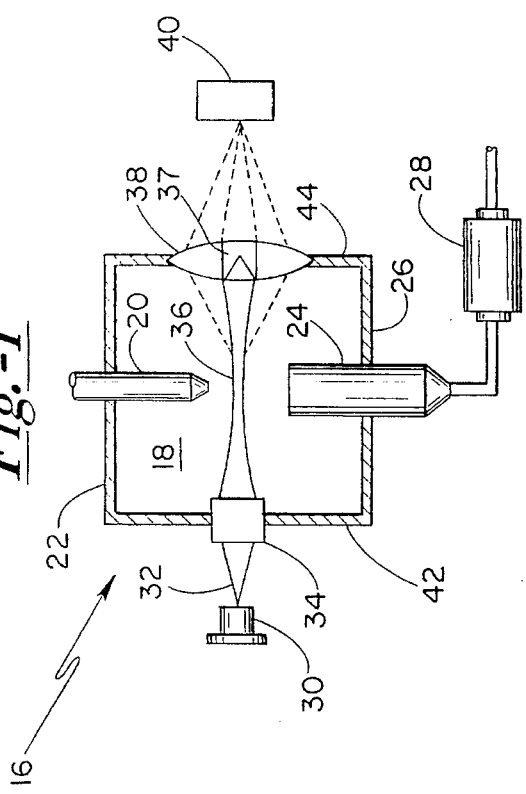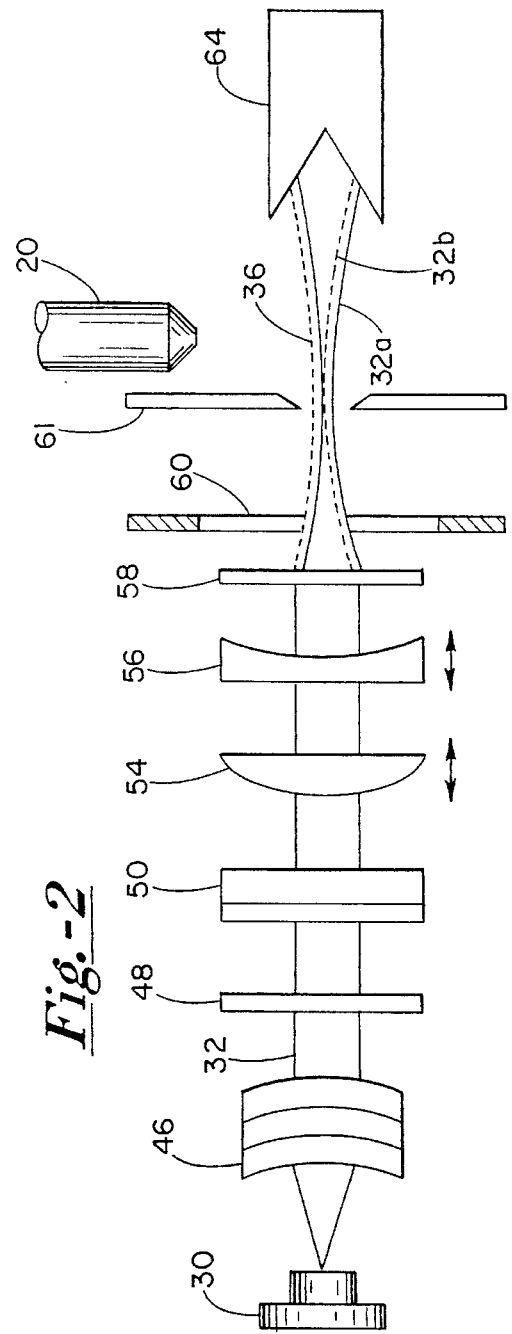

THREE DIMENSIONAL BEAM INTENSITY PROFILE

INTENSITY PROFILE

APPARATUS FOR MEASURING PARTICLE SIZES AND VELOCITIES

BACKGROUND OF THE INVENTION

This invention relates to the detection and characterization of small particles, aerosols or other elements in a fluid stream, and more particularly to determining particle velocities, as an end in itself and for determining aerodynamic particle sizes and other particle characteristics.

Optical measurements of particle velocities are widely used in studies of gas flows and in particle dynamics. Particle size measurements are employed in a variety of fields involving the study and monitoring of pollution and contamination, respirable particle mass, and spray nozzle performance. Techniques have been developed for the empirical estimation of particle characteristics, e.g. composition, mass and index of refraction, based on velocity and size measurements.

One well-known velocity measurement technique is laser Doppler velocimetry (LDV) also known as laser Doppler anemometry. According to this approach, particles or other elements simultaneously scatter light from two coherent beams with different angles of incidence. A photodetector receives the scattered light and generates a frequency representing the heterodyne difference in Doppler shift frequencies produced by particle motion relative to the beams. LDV is useful, yet requires careful alignment of the beams. Beam coherency must be maintained. Sophisticated and expensive signal processing techniques are required to measure the short frequency bursts produced by the particles. Phase Doppler anemometry also is used in measuring the sizes of spherical droplets. This requires multiple photodetectors aligned at precise angles, and complex signal processing circuitry to determine phase relationships of scattered light signals.

Another well known velocity measuring technique is time-of-flight velocimetry, also referred to as transit time, two-spot, or two-focus velocimetry. According to this method, two beams of electromagnetic radiation with radially symmetrical intensity distributions are directed through a particle sampling volume. A particle, when passing through both beams, generates two pulse signals. A timing signal is initiated coincident with the first pulse and terminated coincident with the second pulse, for a "time of flight" measurement over a known distance, thus to yield particle velocity. This approach provides better signal-to-noise ratios than LDV for certain applications, and does not require light beam coherence. Further, since it involves measuring time rather than frequency, the typical time-of-flight application can employ lower cost signal processing circuitry. U.S. Pat. No. 4,251,733 (Hirleman, Jr.) describes a time-of-flight system that measures two velocity components and uses scattered radiation for estimating particle sizes. This system requires precise beam geometry, and analysis of the optical signals as to pulse width and pulse amplitude ratios.

An article by Mark P. Wernet entitled "Four-Spot Laser Anemometer and Optical Axis Techniques for Turbine Applications" (International Congress on Instrumentation in Aerospace Simulation Facilities—1987, pages 245–254) describes a four-spot time-of-flight laser anemometer system. This system requires two pairs of laser beams, with each pair having orthogonally polarized beams. The system employs four photodetectors, each configured to selectively receive light from one of the beams comprising the pairs. Signals from the two photodetectors corresponding to a given pair are subtracted to produce timing signals.

The time-of-flight technique is subject to error. For example, a particle can produce a signal sufficient for detection when passing through one of the beams, but not the other, either due to its trajectory or because of its size being at the borderline of detection. This occurrence, called a "single trigger event", can lead to an erroneous time-of-flight measurement when a signal from the arrival of a second particle is mistakenly identified as the departure signal of a first particle.

A second error for the two-spot technique occurs when one or more additional particles cross the beams between the initial and final signal for an initial particle. This creates ambiguity as to which pulses are associated with each particle for timing measurements, and is known as a "coincidence event". The frequency of this error is greatest when only one photodetector collects light scattered from both beams. However, since coincidence events often occur when a faster travelling particle overtakes a slower particle during its flight between the beams, these errors can arise even when each beam is paired with its own light-photodetector.

Several patents to Batchelder et al, including U.S. Pat. Nos. 5,037,202; 5,061,070; and 5,133,602 disclose optical systems with partially overlapping beams directed through a fluid stream for measuring particle size, refractive index and position within the stream or flow. This system is based on an interferometric technique for sequentially measuring the change in the phase of each coherent light beam as particles are transported in the fluid. Two detectors simultaneously receive light emerging from the flow and provide their outputs to a summing amplifier for determining extinction, and to a difference amplifier for determining phase shift. Position measurement requires detailed analysis of the shapes and relative amplitudes of the phase signal.

It is well known to employ scattered or extinguished light to measure the "optical size" of individual particles. Optical size depends primarily on physical size, index of refraction and shape of the particle. Typically a gas containing the particles is drawn into a chamber to move the gas stream and particles through a region of substantially uniform light beam intensity. Light scattered by the particles is focused onto a photodetector, with the photodetector amplitude indicating optical size. Alternatively, in the light extinction approach, the photodetector output varies to indicate the reduction in beam power due to the particle.

Particle sizes also are determined based on their aerodynamic behavior. An aerodynamic particle size measuring device operates on the principle that a particle's velocity in an accelerating flow of air or other gas depends on its aerodynamic diameter. Aerodynamic diameter information is useful, in that aerosol behavior in the human respiratory system varies with aerodynamic particle diameter. Typically the device measures particle velocity in an accelerated flow, e.g. near a nozzle, near obstructions in the gas flow path, along curvature of the flow path or where two gas streams intersect. When a particle enters an accelerated flow, the "relaxation time" of its velocity—i.e. the time necessary for the particle velocity to coincide with velocity of the surrounding gas—depends on its mass, physical size and shape. When particle density is known, the measured aerodynamic size can be used to estimate particle mass. U.S. Pat. No. 3,854,321 (Dahneke) describes a particle beam device that includes a technique for sizing the particles.

Any of the above techniques for optical measurement of the velocity of bodies in a gas can be coupled with an acceleration of the gas flow in order to measure the aerodynamic sizes of the bodies. However, each of these known velocity measurement techniques has drawbacks associated with complexity and cost, or with measurement accuracy or errors due to coincidence and single trigger events.

Presently, the time of flight or two-spot method is preferred for measuring velocities in aerodynamic particle size measurement, since the signal processing is simpler and less costly. However, the velocity measuring errors described above are not only present in an aerodynamic size measuring device, but are amplified as to their effect, since particle mass varies with the cube of the aerodynamic diameter. Random errors can be mistakenly assumed to be large sized particles, and thus contribute to a disproportionately large error in measured mass. This error is sufficiently serious to prevent the use of aerodynamic particle size measuring in certain applications, such as determining cumulative erosol mass.

To address these errors, Heitbrink and Baron (*An Approach To Evaluating and Correcting Aerodynamic Particle Size or Measurements for Phantom Particle Count Creation*, American Industrial Hygiene Association Journal, July 1992, pp. 427–431) discuss a method of using two signal processors: a small particle processor and a large particle processor. These processors overlap in the aerodynamic particle diameter range of 5.2–15.4 micrometers.

The difference in particle counts in the overlap region is used to estimate an upper limit in the number of phantom particles from the small particle processor. The authors caution that correlation does not remove statistical noise caused by the detection of phantom particles, and further advise that the large particle processor responds to coincidence by underestimating the particulate concentration.

Therefore, it is an object of the invention to provide an optical particle characterizing system employing the time-of-flight technique in a manner to enhance reliability by avoiding the errors traditionally associated with this technique.

Another object is to provide, in time-of-flight velocity systems and in aerodynamic particle size measuring systems, signal processing circuitry to improve correction for particle coincidence and single trigger events, thus to improve measurements of particle concentration.

Another object is to provide a system for characterizing particles as to size, velocity and other traits over a wide dynamic range of electro-optic signals.

A further object is to provide an aerodynamic particle measuring system in which particle mass values are considerably more accurate, due to the reduction in velocity measurement errors.

Yet another object is to provide an optical system for determining a particle's optical size and aerodynamic size, and for applying these sizes in combination to determine further particle characteristics.

SUMMARY OF THE INVENTION

To achieve these and other objects, there is provided an apparatus for measuring velocity of discrete particles or other elements carried in a fluid stream. The apparatus includes a means for generating radiant energy and for directing the radiant energy in a path that intersects the fluid stream to form a measuring volume. Further means selectively control the intensity of the radiant energy to vary the intensity in a flow measurement direction in the measuring volume. Accordingly, the measuring volume includes a first region of intensity, a second region of intensity downstream of the first region, and an intermediate region of intensity between and contiguous with the first and second regions. Each of the first and second regions has an intensity level greater than that of the intermediate region.

A light receiving means receives at least a portion of the radiant energy that emerges from the measuring volume. The receiving means includes detecting means for generating an electrical signal responsive to received radiant energy. The electrical signal has a background level when no particle is present in the measuring volume. The electrical signal also has a time-dependent profile corresponding to the passage of one of the discrete elements through the measuring volume. The time-dependent profile includes first and second peaks corresponding respectively to element travel through the first and second regions. The signal further includes an intermediate profile segment between the peaks having an intermediate level between the background level and the level of each peak. The intermediate profile segment corresponds to element travel through the intermediate region.

Means are provided for measuring a time of travel for the element from a first point in one of the regions to a second point in another one of the regions, based on a time-dependent distance from the first point to the second point, and for generating an element velocity value based on the time-dependent distance. Means are provided for generating a threshold signal representing a predetermined-level of departure from the background level. Means monitor the time-dependent profile with respect to the threshold signal. The element velocity value is validated only if the threshold signal, over the entire time-dependent distance, remains between the background level and the time-dependent profile.

Because the intensity regions are contiguous, an element in the flow produces a continuous, uninterrupted signal as it is transported through the measuring volume.

The light-receiving means can collect light scattered by the element, in which case the levels of the first and second peaks are greater than the level of the intermediate profile segment, and these levels all are greater than the background level. In a preferred application, the receiving means includes collection optics having a focal location in the measuring volume, a detector means positioned to receive forward scattered light from the collection optics, and a light stop to prevent direct passage of radiant energy to the detector means. Back-scattered or side-scattered light also can be sensed, if desired.

Alternatively, the system can be based on light extinction, in which case the levels of the peaks are less than the level of the intermediate profile segment, which in turn is less than the background level.

In either event, if the intermediate profile segment crosses the threshold signal, the element velocity measurement is rejected. In physical terms, a particle or other light scattering element must be of sufficient size to scatter (or extinguish) at least a predetermined amount of light during its traverse through the measuring volume. Otherwise, it will not be used for generating velocity data.

Advantageously the measuring volume is formed using two laser beams, each with a substantially Gaussian intensity profile. The beams overlap one another peripherally, to ensure continuity of the laser light over the viewing volume, particularly for threshold signal continuity. At the same time, the overlap remains peripheral in nature, i.e. sufficiently small to insure a discernable difference between the peaks and the region between peaks.

The time-dependent amplitude profile of the electrical signal is closely related to the position-dependent intensity profile across the measuring volume. This fact is used to advantage by the preferred signal processing techniques. The time of travel is measured by generating a difference signal based on subtracting a time-delayed profile (the time-dependent profile delayed by a predetermined amount) from the original time-dependent profile. The difference signal includes two negative going zero transitions, which correspond to the particle crossing the first and second regions of the measuring volume. The zero transitions afford more accurate time/velocity measurement, since they are less subject to error from variations in peak width and peak amplitude. In the preferred embodiment, means for simultaneously producing a number of selectable delays, such as an electronic tapped delay line, or a shift register, are used to derive the various signals. This allows the difference signal, summed signal, and amplitude signal to be optimally positioned in time with respect to each other by compensating for delays imposed by other signal processing components, such as filters and amplifiers.

The time-dependent profile and a time-delayed profile further are summed to provide a summed profile. The summed profile is continually compared to the threshold signal. So long as the summed profile exceeds the threshold signal, a comparator generates a digital logic level indicating the presence of one or more particles in the measuring volume. This digital logic signal is referred to as the gate signal. When the summed profile becomes less than the threshold signal, the gate signal ceases to be true and either the particle data is accepted as valid if criteria for the difference signal are met, or the particle data is rejected if the difference signal fails its criteria.

The system includes further digital logic to insure against single trigger and coincidence errors. In particular, the threshold or gate signal, when active, provides a window during which all negative-going zero transitions are counted. For any count other than two, the resulting velocity value (if any) is rejected. If desired, rejected episodes including single trigger events, coincidence events, or both, can be used to determine information other than velocity, e.g. particle number concentration within the fluid stream.

As an alternative to the above-discussed difference signal, the time-dependent profile can be differentiated to provide the pair of negative-going zero crossings. However, differentiation results in additional high frequency noise that requires more stringent low pass filtering of the signal to avoid degraded performance.

The threshold signal must be of sufficient magnitude to minimize the impact of noise, yet can be relatively low compared to expected levels for the peaks and intermediate profile segment. This, in combination with reliance on zero crossings for the timing signals, minimizes any error due to signal amplitude variance. Since any given range of particle sizes results in a much larger range of signal amplitudes (due to the exponential relationship of scattered light to particle size), signal processing relatively independent of amplitudes results in a larger available range of measurable particle sizes. Moreover, after the zero crossing signals are generated, large amplitude signals can be clipped without affecting the timing and threshold crossings.

According to the present invention, aerodynamic particle size measuring is substantially improved, not only due to more accurate velocity measurements, but also because aerodynamic size measuring (based on velocity) and optical sizing (based on amplitude) are performed nearly simultaneously. This yields a reliable pairing of the signal amplitude and time-of-flight measurements for each particle, with no ambiguities due to single trigger and coincidence episodes. This affords several advantages not found in conventional instruments. First, measurement of both the aerodynamic size and the optical size can lead to useful inferences about a particle's index of refraction and material composition. Thus, utility is enhanced for measuring specific materials within a background of ambient aerosols, e.g. detecting pollens, coal dust particles, or chemical and biological agents, in a background of water droplets or soil dust.

Secondly, the dual size measurement can enhance the range of particles under investigation. A substantial range of particles, too small for aerodynamic sizing, are readily detected and sized by optical means. Thus, the combination of these approaches augments the range of particles which can be sized in any single system.

Thus in accordance with the present invention, selective control of energy intensity throughout a measuring volume and selective processing of the electrical signal generated when a particle crosses the measuring volume, lead to more accurate time-of-flight velocity determinations, more accurate aerodynamic particle size measuring, and enable empirical determinations of particle characteristics through combined aerodynamic and optical particle sizing.

IN THE DRAWINGS

For a further appreciation of the above and other features and advantages, reference is made to the following detailed description and to the drawings, in which:

FIG. 1 is a diagrammatic view of an aerodynamic particle measuring system constructed according to the present invention;

FIG. 2 is an enlarged partial view of the system showing beam generating features;

DETAILED DESCRIPTION OF THE PREFERRED EMBODIMENTS

Figure 3:
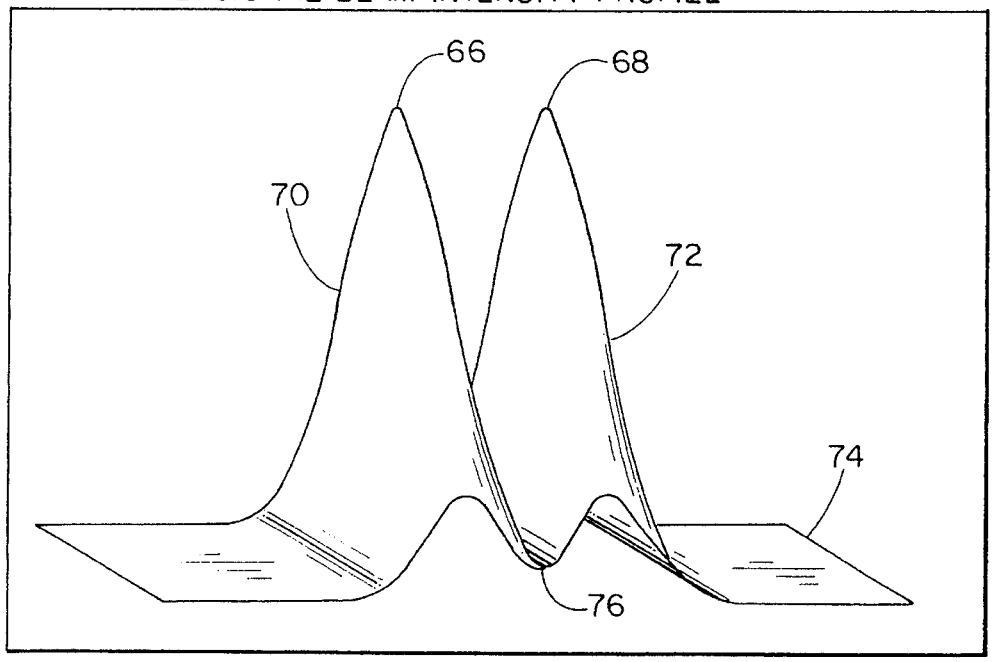
FIG. 3 is a three-dimensional radiation intensity profile of a pair of beams generated using the system.

Turning now to the drawings, there is shown in FIG. 1 an electro-optical system 16 for recognizing and characterizing particles in a gas stream. System 16 employs two interacting subsystems including a gas flow system for generating a flow or stream of a gas and an optical system for viewing the gas stream and characterizing particles carried in the gas stream.

Considering first the gas flow system, gas (usually air) containing particles is drawn into a chamber 18 through a nozzle assembly 20. Nozzle assembly 20 is built into a top wall 22 of the chamber. An exit conduit 24 is mounted through a bottom wall 26 of the chamber. A pump 28 is operable to draw gas out of the chamber through exit conduit 24, thus to create and maintain a reduced pressure within the chamber for drawing a continuous flow of the gas through nozzle assembly 20 and into the chamber. While the flow of gas is steady in terms of mass transfer, it does not maintain a constant velocity. Rather, the gas stream is accelerated just before entering the chamber from the nozzle assembly. Pump 28 is controlled to maintain a substantially constant flow rate (in terms of volume) and thus also maintains a substantially constant gas flow acceleration at the nozzle exit.

The optical system includes a radiant energy source 30 for generating laser energy. A beam 32 emerging from the source proceeds through beam controlling optics 34, where the beam is selectively shaped and focused along a portion of its path intersecting the gas stream. This region of intersection provides a measuring volume 36 for detecting and characterizing particles. Scattered laser energy emerging from the measuring volume is gathered by beam collecting optics 38 and directed onto a photodetector 40.

Light controlling optics 34 are built into a forward wall 42 of the chamber. Beam collecting optics 38 are built into a rearward wall 44 of the chamber, and contain an opaque light stop or trap 37 aligned to receive the direct beam beyond measuring volume 36. Opaque trap 37 insures that only scattered light is directed onto the photodetector. The walls of chamber 18 are opaque to minimize stray light interference with the generated beam or alteration of readings based on scattered or extinguished light.

Beam generation features of the optical system appear in more detail in FIG. 2. Energy source 30 is a single transverse mode diode laser with electronic power stabilization. The beam configuring optics include a collimating lens 46 to receive laser energy from diode laser 30. Collimating lens 46 has a focal length of approximately 4.5 mm and a numerical aperture of approximately 0.45 to collimate or nearly collimate the diverging beam from the laser. Collimated light is directed to a polarization rotator 48, which adjusts laser polarization with reference to a downstream beam splitter. Polarization is adjusted to be approximately 45 degrees offset from the axis of separation at the beam splitter, which axis is vertical as viewed in FIG. 2.

The light then proceeds to a first cylindrical lens 50 having a vertical focus. Lens 50 is adjustable with respect to the nozzle assembly 20. Lens 50 partially focuses beam 32 to adjust the beam width to approximately 1.1 mm at measuring volume 36. The beam width is horizontal and transverse, i.e. perpendicular to the longitudinal beam propagation path, such that a line in the width direction would appear as a point in FIG. 2.

Light emerging from cylindrical lens 50 encounters a pair of cylindrical lenses at 54 and 56. The axes of lenses 54 and 56 are transverse and horizontal as viewed in FIG. 2, i.e. perpendicular to the longitudinal axis of beam 32 and to the vertical axis of first cylindrical lens 50. Lenses 54 and 56 are adjustable longitudinally with respect to one another and with respect to nozzle assembly 20. Lenses 54 and 56 thus are employed as a cylindrical telescope to adjust the size and position of the vertical focus of beam 32. The preferred beam thickness (vertical direction) within the focal region is 0.06 mm, when measured at the 13.5% intensity points of a beam with an approximately Gaussian vertical intensity profile. The use of two cylindrical lenses 54 and 56 allows compensation for variations in the size of beam 32, due to differences in the divergence angle of the beam as it exits the diode laser. A single cylindrical lens can be used in place of lenses 54 and 56, but with reduced ability to control focal region size and position.

In an arrangement alternative to that shown in FIG. 2, a pair of anamorphic prisms can be used in lieu of first cylindrical lens 50 for controlling the width of beam 32 at the measuring volume. In this arrangement, the beam is approximately collimated when it emerges from the anamorphic prism pair. In this arrangement, the polarization rotator would be positioned downstream to receive light from the anamorphic prisms, as opposed to the positioning of rotator 48 ahead of the first cylindrical lens in FIG. 2.

Downstream of the cylindrical lenses is a calcite beam splitter 58, for separating beam 32 into two beams 32a and 32b, transversely spaced apart from one another as to their centers, yet overlapping one another along respective radially peripheral regions, e.g. at intensities less than about 5% peak amplitude. Beam splitter 58 has an optical axis which is selectively oriented to separate beams 32a and b in the vertical direction. The calcite plate thickness is selected to determine the spacing of beams 32a and 32b. The preferred separation between beam centers is approximately 0.08 mm. Beams 32a and b have approximately the same intensity, because of the 45° polarization of the beam, effected by polarization rotator 52.

Beams 32a and b enter chamber 18 through a window 60 mounted within forward wall 42. An aperture 61 minimizes the amount of stray light, e.g. scattered from the optical elements or their edges, that can enter the chamber. Window 60 is sealed to prevent stray contaminants from entering the chamber.

Beams 32a and b intersect the gas stream to form measuring volume 36, which is the region common to the beams and to the gas flow. As the beams emerge from the measuring volume, they encounter a light stop 64. The light stop absorbs light to prevent the beams from directly reaching a downstream photodetector, which would undesirably increase noise in the electrical signal output of the photodetector.

When a coherent energy source such as diode laser 30 is used to produce overlapping beams, the region of beam overlap normally produces interference fringes, which would add undesirable structure to the beam profile. Calcite beam splitter 58 produces two beams which are orthogonally polarized relative to each other, thus to avoid formation of interference fringes. As an alternative to using the calcite beam splitter, the beams could be formed of incoherent light. Another alternative is to employ a beam separation technique involving a difference in path lengths to the measuring volume, which difference is longer than the coherence length of the light source.

FIG. 3 illustrates an intensity profile, in three dimensions, of beams 32$a$ and $b$ at the measuring volume. The beams have the same intensity profile. More particularly, each beam has a substantially Gaussian intensity profile with respective maximum intensities 66 and 68 at the respective beam centers, and intensity levels that decrease in all directions away from the center, forming respective peaks 70 and 72. The substantially flat region around the peaks, indicated at 74, represents a background level of intensity beyond the beam peripheries. An intermediate intensity level 76 is at least approximately centered between peak maximum values 66 and 68. While substantially less than these maximum values, level 76 is substantially greater than the background level.

Figure 4:
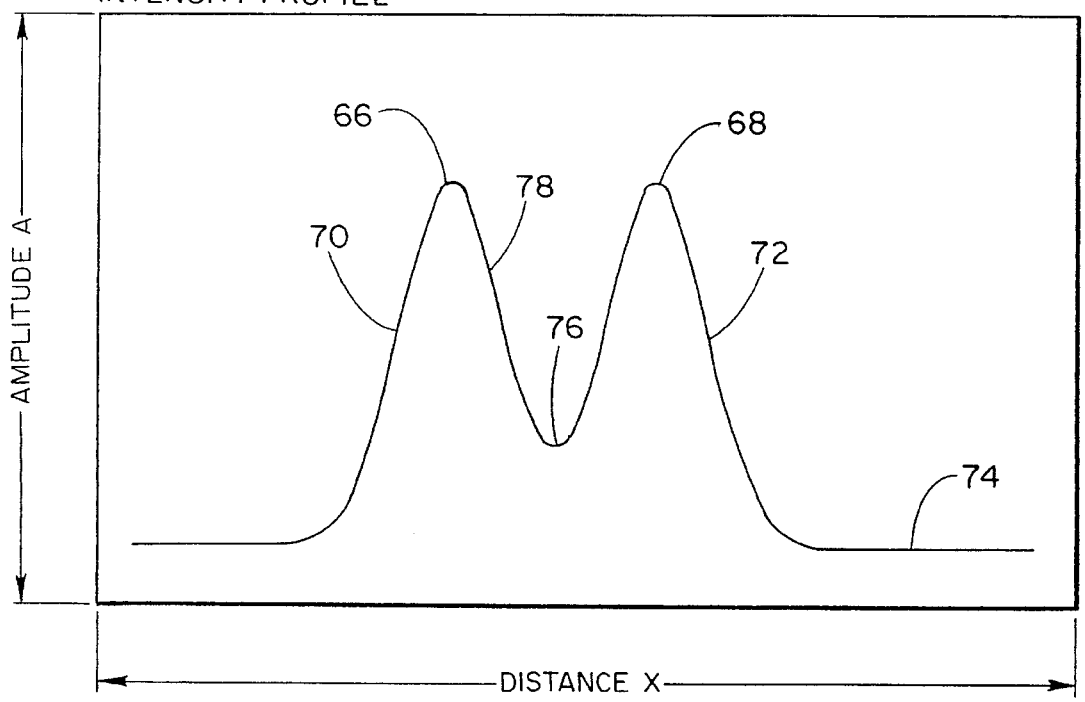
FIG. 4 is a corresponding planar intensity profile.

FIG. 4 shows a planar intensity profile 78 equivalent to the profile in FIG. 3 taken in a plane that bisects peaks 70 and 72. When this intensity profile follows a Gaussian distribution, the profile is defined according to the expression $$\text{where} \quad a = \frac{-(x + d/2)}{2s^2}$$
$$\text{and} \quad b = \frac{-(x - d/2)}{2s^2}$$

where A is the peak intensity of each beam (since the two beams are equal); x measures distance, and is zero at the center between the peaks; d is the distance between beams 70 and 72, more precisely the distance between their centers; and s is the standard deviation of the Gaussian beam profile. The term "e" is the number whose natural logarithm is 1.

The ratio of d to s determines the relative amplitude of intermediate level 76 with respect to peaks 70 and 72. In the most highly preferred embodiment, the ratio of d/s is approximately 5, with the beam separation d being approximately 80 micrometers and the beam width standard deviation s being approximately 15 micrometers. A range of useful limits surrounds the preferred values. In particular, a d/s ratio in the range of from 2.2 to 6.5, for which the intermediate level ranges from 0.01 to 0.99 of the peak maximum values, has been found satisfactory.

While an approximate Gaussian profile is preferred, it is to be recognized that any beam or combination of beams that affords a smooth beam profile in the measuring volume is satisfactory, so long as its intensity profile includes two discernable peaks separated by a discernable minimum between the peaks and substantially greater than threshold intensity levels.

Figure 5:
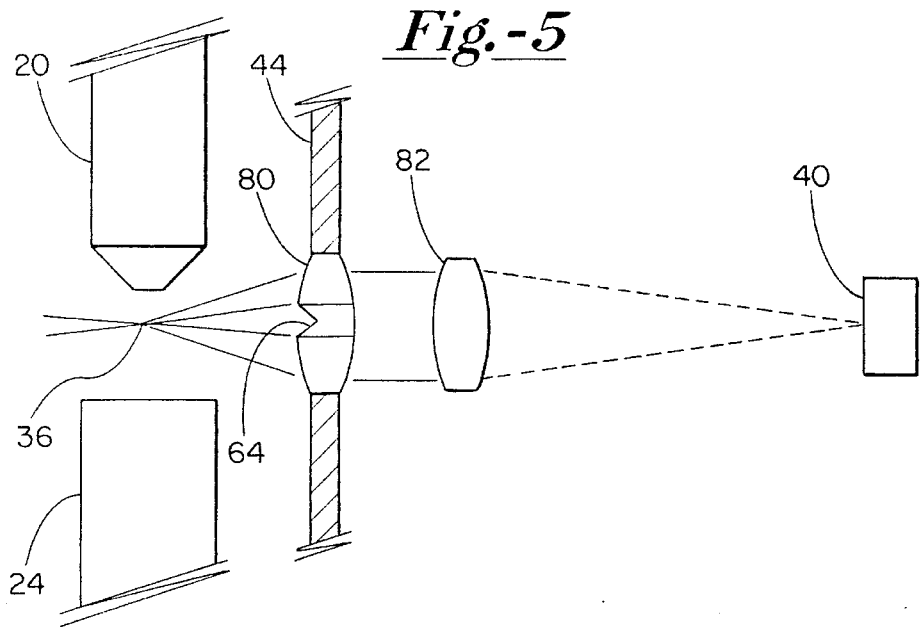
FIG. 5 is a partial view of the system showing light collection features.

Particles passing through measuring volume 36 scatter light in all directions throughout chamber 18. However, as seen in FIG. 5, only forward scattered light is collected and used for particle measurement. Forward scattered radiation proceeds through a pair of aspheric lenses 80 and 82. Upstream lens 80 is mounted within rearward wall 44 of the chamber, in a manner that seals the lens within the wall. Lenses 80 and 82 image the region of the measuring volume onto the photodetector 40, for maximum sensitivity to intensity changes caused by particles traversing the viewing volume. In the preferred embodiment, each of lenses 80 and 82 has a numerical aperture of approximately 0.6.

Light gathered by lenses 80 and 82 is provided to silicon avalanche photodetector 40, which includes circuitry for controlling its bias voltage and a preamplifier that converts current to voltage. The photodetector output is a voltage signal based on received forward scattered radiation. The detector preamplifier gain is set to provide that the optical signal from the largest expected particle of interest does not saturate the preamplifier.

Several alternative light collection schemes can be implemented in lieu of this system, e.g. a reflective system based on mirrors, large fiber optic or solid glass "light pipes" for transmitting collected light to the photodetector, or direct (lensless) scattering onto one or more photodetectors. Also, if desired, a second photodetector can be configured to sense amplitude noise in the light source. A signal from this detector is then subtracted from photodetector 40 to cancel amplitude noise. Finally, photodetector 40 can be configured to generate a signal based on extinction, i.e. the degree to which a particle in the measuring volume reduces light received by the photodetector. In this event there is no light stop, and light of beam 32 is provided in a direct path to the photodetector.

Figure 6:
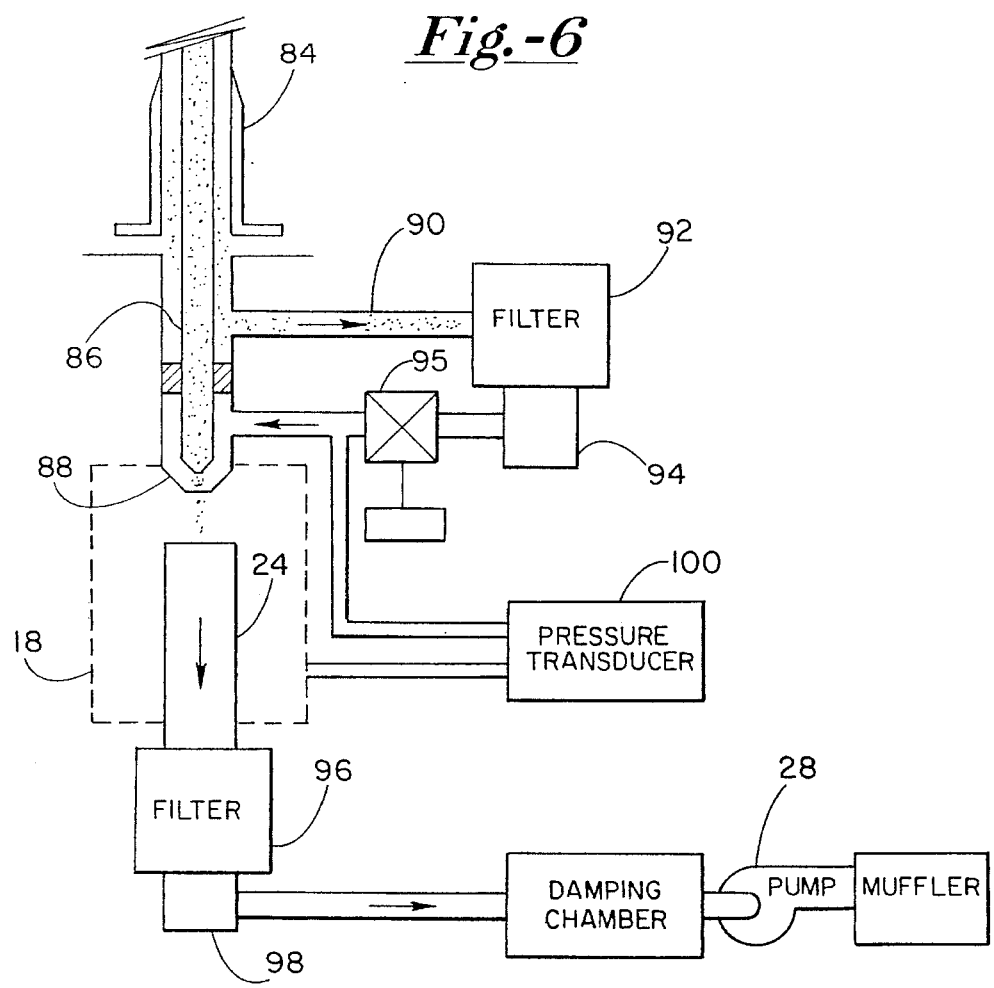
FIG. 6 is a partial view of the system showing features for generating a gas stream.

As seen in FIG. 6, the gas flow system includes an inlet conduit 84 receiving the particle-containing gas, typically air. Coaxial nozzle assembly 20 includes an inner nozzle 86 and an outer nozzle 88 concentric about the inner nozzle. Thus the nozzle assembly forms two flow paths, an inner circular path surrounded by an annular flow path. Air in the outer path is directed along a conduit 90 to a high efficiency filter 92 for removal of substantially all of the particles. A flow meter 94 is positioned immediately downstream of filter 92 to monitor the sheath flow. Downstream of the flow meter is a sheath flow valve 95, adjusted such that the annular sheath air flow is 80% of total flow, with the remaining 20% moving through inner nozzle 86. In the preferred embodiment, the inner nozzle flow rate is 1 liter per minute, with a sheath flow rate of 4 liters per minute of filtered air. The inner nozzle diameter is approximately 0.8 mm, and the outer nozzle diameter is approximately 1 mm, with the annular space between nozzles being approximately 0.75 mm. Pump 28 draws air from the chamber to reduce the pressure to about 125 cm of water below ambient inlet pressure, which maintains air velocity at the exit to the nozzle assembly at approximately 150 meters per second. At the downstream end of exit conduit 24 is a filter 96 followed by a flow meter 98 for measuring total flow. Flow meters 94 and 98, in combination with a pressure transducer 100, maintain the desired ratio of sheath flow to inner nozzle flow by adjusting valve 95.

Figure 7:
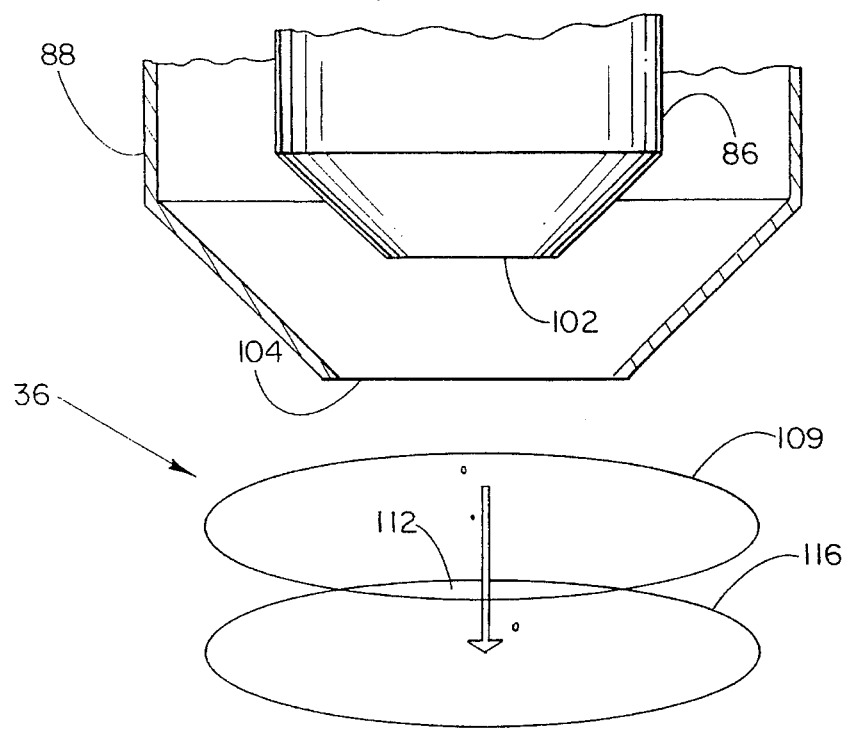
FIG. 7 is an enlarged partial view of FIG. 5 illustrating a measuring volume formed by the beams, and a nozzle exit upstream of the measuring volume.

FIG. 7 shows the exit region of the nozzle assembly, including an exit 102 of the inner nozzle and an exit 104 of the outer nozzle. Measuring volume 36, shown in transverse profile, is disposed immediately downstream of the nozzle exits. Because cylindrical lenses 54 and 56 focus beam 32 only in the direction of particle motion, each of beams 32$a$ and $b$ has a highly ellipsoid profile, in which major axis (horizontal as viewed in FIG. 7) is, for example, at least ten times the length of its minor axis (vertical direction). More preferably, the aspect ratio is approximately 18:1. As a result, measuring volume 36 is narrow in the flow measurement direction (vertical in FIG. 7) while being sufficiently wide to capture particles moving with the air stream. Moreover, the essentially particle-free annular air sheath tends to confine particles to the center of the measuring volume. Consequently amplitudes of light at photodetector 40 tend to vary with changes in particle optical sizes, rather than deviations of particle paths from the center of the measuring volume. As indicated in FIG. 7, a relatively small, peripheral overlap of the beams is sufficient to provide an intermediate minimum amplitude well above background intensity. Beams with circular rather than elliptical profiles can be used, although elliptical profiles are preferred.

The radiation intensity profile downward through the measuring volume preferably reflects a substantially Gaussian intensity distribution for two peaks that overlap to create a recognizable minimum between peaks. As a result of this distribution, each particle when traversing the measuring volume tends to scatter light in a time-dependent amplitude sequence that matches the intensity profile. The corresponding output of the preamp for photodetector 40 is a time-dependent voltage profile that likewise matches the intensity profile as seen at 106 in FIG. 8. A background level 108 represents a voltage level when no discernible particle is within the measuring volume. However, as a particle is carried through the measuring volume it first encounters beam 32a, which can be considered as a first region 109 of the measuring volume. As it proceeds through the first region toward the center of beam 32a, the particle scatters steadily increasing amounts of light, causing time-dependent voltage profile 106 to rise to a maximum level 110 which corresponds to the center of beam 32a. Further particle movement reduces the scattered light, with reduction continuing as the particle enters a second region 112, i.e. the intersection of beams 32a and b. The intensity of scattered light (and thus the voltage) continues to decline in spite of the overlap because of the steep decline in intensity radially away from the center of each beam. An intermediate voltage level is indicated at 114, well above the background level. Voltage increases steadily as the particle moves out of the overlap region and into a third region 116 corresponding to beam 32b. Again, a maximum voltage 118 corresponds to the particle being at the center of beam 32b. Finally, voltage decreases as the particle exits the measuring volume.

Figure 8:
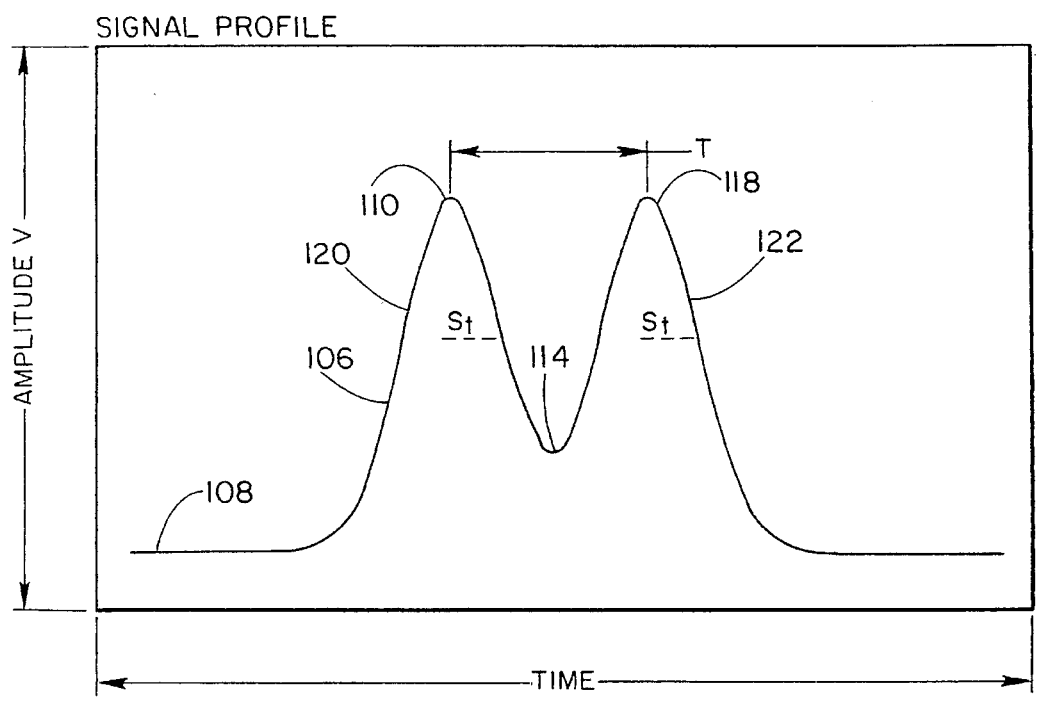
FIG. 8 is a schematic view of a time-dependent amplitude profile corresponding to a single particle passing through the measuring volume.

The mathematical expression for the voltage waveform produced by a particle passing through the measuring volume is analogous to the expression for the light intensity profile. Thus, by substituting a peak voltage V for intensity A, a time variable t for the position variable x, a time separation T for distance separation d, and a time-based standard deviation $s_t$ for the profile standard deviation, the previous expression applies to the voltage waveform (FIG. 8). The central minimum 114 corresponds to time t=0, the peak voltages 110 and 118 occur at approximately plus and minus T/2, and $s_t$ indicates the standard deviation of each of the overlapped Gaussian profiles.

Figure 9:
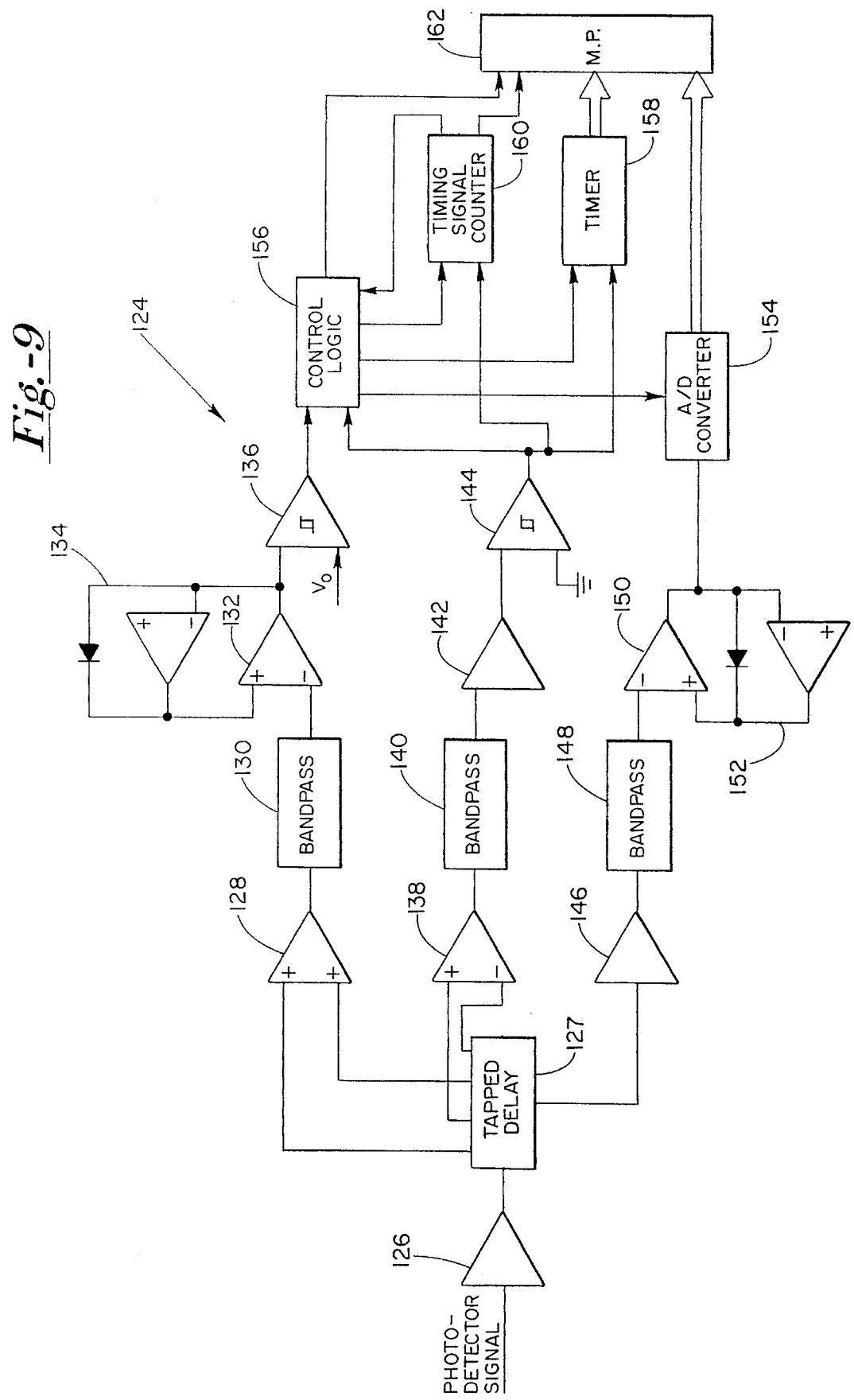
FIG. 9 is a schematic view of system circuitry for processing electrical signals generated by a photodetector responsive to forward scattered radiation.

Time-dependent profile 106 is processed to obtain particle time-of-flight values; to determine signal amplitudes; to establish a threshold or gate for validating time-of-flight values, and for rejecting potential time-of-flight values based on incomplete signals or signals from multiple particles temporally overlapped in the measuring volume. FIG. 9 schematically illustrates a signal processing circuit 124 which receives the output of photodetector 40, more specifically preamplifier 126 of the photodetector. The photodetector output is provided along three paths of circuit 124 for: deriving the gate signal; deriving the timing or time-of-flight signal; and determining signal amplitude. Along each of these paths, signals are low pass filtered for a bandwidth near the frequency band that contains signals from fast particles, and high-pass filtered to remove any low frequency drift or noise, such as from mechanical vibration or from AC power line voltages. The preferred high-pass filter cut-off is approximately 1 KHz. The preferred low-pass filter cut-off is approximately 3 MHz for the difference signal, and 500 KHz for the sum and amplitude signals.

Several signals are derived from time-shifted versions of the photodetector output. The time-shifted signals are obtained from a tapped, analog delay line 127. Signals are selected for incremental delay taps to achieve the desired functions and to compensate for timing skews, such as those due to filters and amplifiers. Concerning first the analog sum signal, the photodetector output is delayed a predetermined amount, equal to one-half the expected time of flight of the fastest particle of interest. Typically this is a particle travelling at or near the maximum expected gas flow velocity. In the present embodiment, the delay is about 300 nanoseconds. The output of delay line 127, for convenience called a "time-delayed profile", is provided to an operational amplifier 128. The original time-dependent profile also is provided to amplifier 128. These profiles are summed. The output is low-pass filtered and high-pass filtered as represented by a band-pass filter 130. The band-pass filter output is provided to a fast-recovery clipping amplifier 132 with feedback in the form of a base line clamping circuit 134. The clamping circuitry prevents changes in the signal base line, which otherwise might occur from high-pass filtering many, closely spaced signals.

The output of amplifier 132, which can be called a "summed profile", is provided to a comparator 136 The other input to the comparator is a constant threshold voltage $V_0$. So long as the summed signal exceeds $V_0$, the comparator output is the "high" logic level. Should the summed signal fall below $V_0$, the comparator output switches to the "low" logic level. The comparator output is the gate signal used to qualify timing measurements.

The timing signal also is based on the time-dependent profile and the time-delayed profile. These signals are provided to an operational amplifier 138, with the time-delayed profile being subtracted from the time-dependent profile. The output of amplifier 138 is high-pass filtered and low-pass filtered at band-pass filter 140 and provided to a fast recovery clipping amplifier 142. The output of amplifier 142, which can be called a difference signal, is provided to a timing comparator 144. Unlike the summed profile, the difference profile is a bipolar signal (i.e. with no average DC value) and does not require baseline clamping. The other input to comparator 144 is a ground or zero voltage input, for recognizing negative-going zero transitions of the difference profile. The output of comparator 144 switches from the high logic level to the low logic level responsive to these crossings, and of course switches from low to high responsive to positive going zero transitions. The comparator has hysteresis to prevent excessive switching due to noise.

The time-dependent profile also is processed to determine signal amplitude. An output from delay line 127 is selected so that a peak of the voltage profile approximately coincides with a zero crossing of the difference signal. The time-dependent profile with this selected delay is provided to buffer amplifier 146, high-pass and low-pass filtered as indicated at 148, then provided to a logarithmic amplifier 150 that includes a baseline clamping circuit 152. The logarithmic amplifier output is provided to a "flash" analog-to-digital converter 154, which is triggered by a difference signal zero crossing. As implemented, the first zero crossing is made to coincide with the first peak of the signal profile. The A/D output is a digital representation of amplitude and is stored along with the time-of-flight measurement. If desired, a peak hold circuit and a slower A/D converter may be used in lieu of A/D converter 154.

Figure 10:
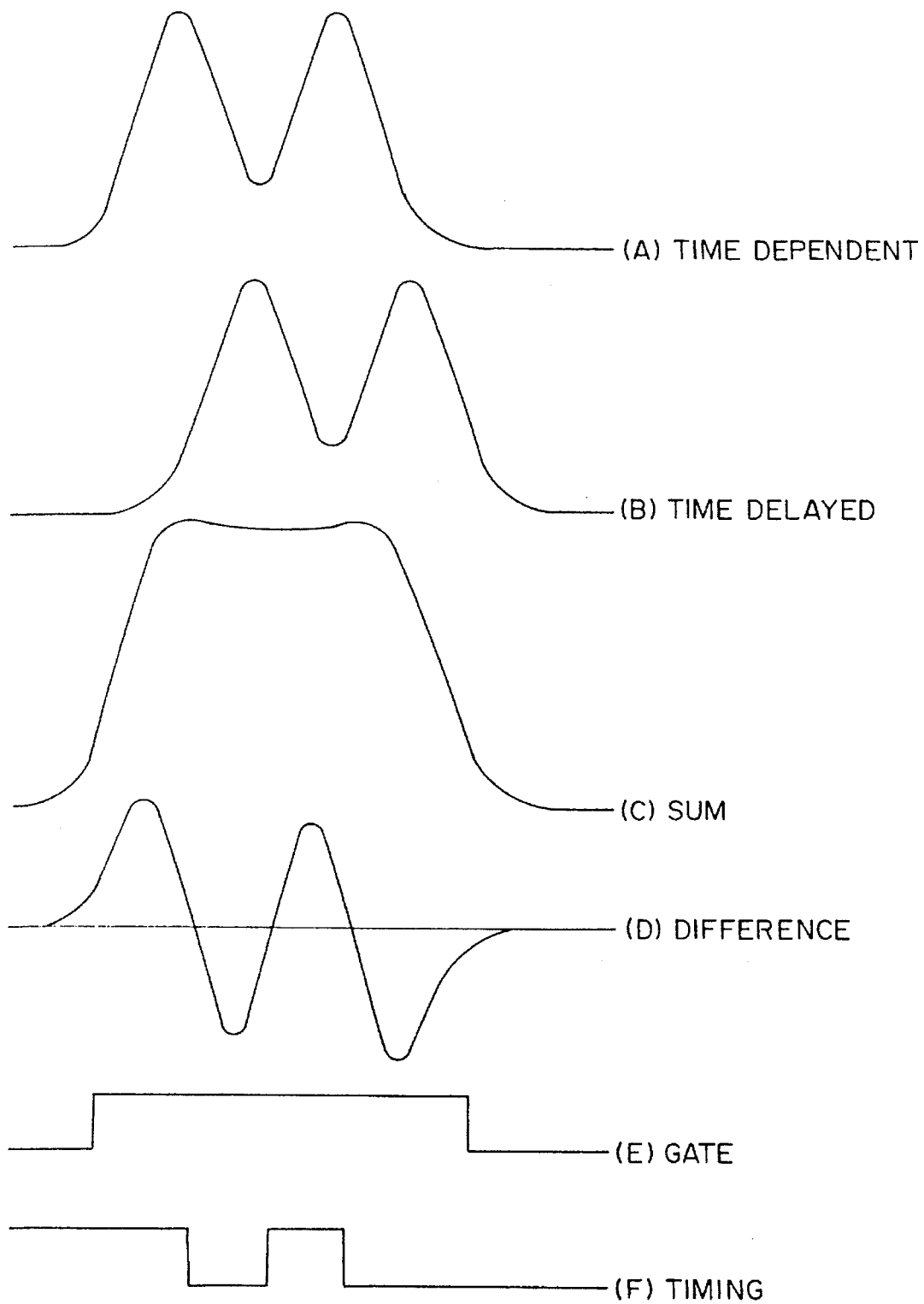
FIG. 10 is a timing diagram illustrating the time-dependent amplitude profile and several signals generated based on the time-dependent profile.

FIG. 10 is a timing diagram illustrating the signals just discussed. The time-dependent and time-delayed voltage profiles are shown respectively at A and B. The summed profile, shown at C, is used to trigger the gate signal E based on the level of As shown, the gate signal remains high throughout the time of the particle's travel through the measuring volume. A velocity measurement based on that particle is qualified when exactly two negative-going zero transitions of the time-of-flight signal are recorded while the gate signal is high.

The difference profile, shown at D, triggers the timing signal at F. The two negative-going zero crossings of the difference signal trigger high-to-low transitions of the digital timing signal. The transitions do not coincide with the peak or maximum values of time-dependent profile peaks 120 and 122. Rather, each zero crossing coincides with a point along the downward slope following the maximum value. However, since both zero crossings are offset by this amount and the time-of-flight (velocity) values are based on the difference in time between zero crossings, the lack of coincidence with maximum peak values does not reduce accuracy. In fact, because of the relatively fast slew rate of the signal through the zero crossings, accurate time based on the zero crossings is easier to achieve than timing based on direct measurement of peak-to-peak times.

The peaks of the photodetector signal correspond to zero values of the mathematical derivative of that signal, and thus the peak-to-peak times correspond to zero crossings of the differentiated signal. However, electronic differentiation results in increased amplification of high frequency noise, which degrades the time measurement. The approach described here replaces differentiation with a finite time differencing. This substantially reduces the noise effects of differentiation, while it is limited in the range of waveform periods, and thus particle velocities, that can be effectively processed. As described, the circuit can cover a velocity range of approximately 10 to 1. This range may be extended to cover greater velocity variations by implementing a series of electronic delay times, such that each delay time is appropriate for a different range of signal periods. Criteria, such as the duration of the gate signal, are than used to select the delay time for generating the measurement of particle velocity. Since a velocity range of about 5 to 1 is sufficient for typical aerodynamic particle sizing applications, selection of the delay is not needed.

The circuit of FIG. 9 further incorporates digital logic for determining velocities and amplitudes, and for either qualifying or rejecting velocity values. As seen from FIG. 9, the gate signal and timing signal are provided to control logic 156, which is governed by a 250 MHz clock oscillator or timer 158. A timing signal counter 160 accumulates timing signals, and interacts with control logic 156 to count individual pulses over predetermined intervals, such as between the first and second negative-going zero transitions. The timer, counter, control logic, and A/D converter provide their outputs to a processor 162.

Figure 11:
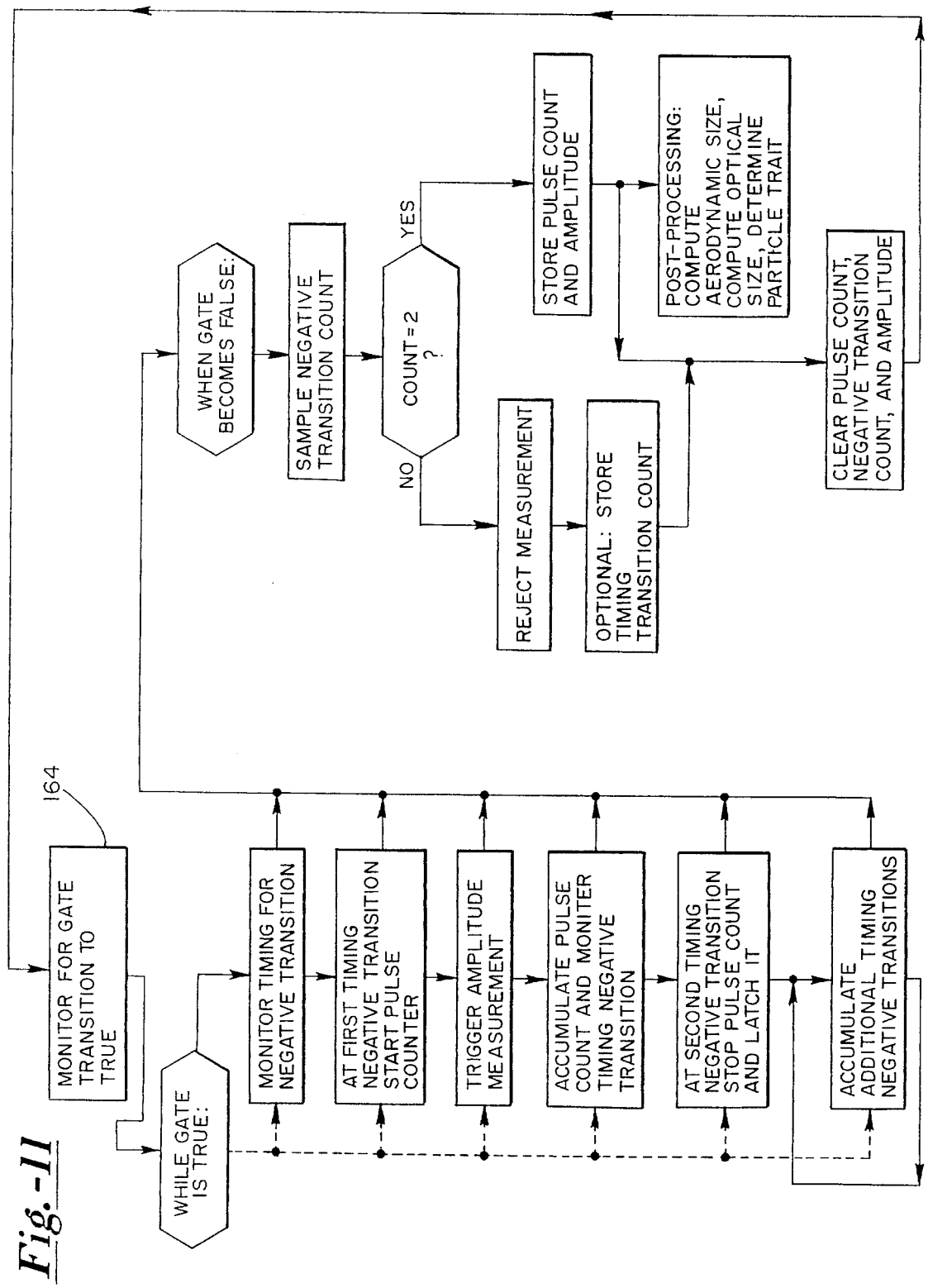
FIG. 11 is a flow chart illustrating signal handling logic of the circuitry.

FIG. 11 is a flow chart illustrating the manner in which values are obtained and validated. As indicated at 164, the control logic continually monitors the gate signal. If the gate signal is true, negative-going transitions in the timing signal are counted and accumulated, regardless of whether the count is equal to one. However, a transition count of one triggers a further step of initiating a pulse count and accumulating the pulse count. The transition count is continually monitored, so long as it remains less than two. When the count of transitions reaches two, the pulse count is terminated.

At this point, it is unknown whether the two transitions were generated by a single particle or a coincidence event. However, eventually the particle (or particles) exits the measuring volume, causing the gate signal to revert to the low logic level. With the gate signal no longer true, the transition count is sampled. If the count equals two, the pulse count is stored as valid timing data and the digital amplitude value also is stored. The transition and pulse counts are cleared and gate signal monitoring continues.

However, if the sampled transition count is not equal to two, the pulse count is rejected as invalid and no timing or velocity data is stored. Transition and pulse counts are cleared. As indicated in broken lines at 166 and as an option, the transition count and amplitude data may be stored for use in determining particle concentration and optical particle size information.

To this point, a transition count of at least 2 has been assumed, and accordingly any rejection of velocity data is based on a coincidence event. In the case of a single trigger event, the gate signal would become true (go high) and the particle would cause a single transition. Then, due to borderline size or trajectory, the particle would exit the measuring volume and cause the gate signal to go low, without causing a second negative going transition. This would trigger a sampling of the transition count and, upon finding a count of 1, the accumulated pulse count would be rejected. The transition count and pulse count would be cleared, and gate signal monitoring resumed.

System 16 is an aerodynamic particle size measuring device, and thus utilizes the valid timing/velocity data to compute the aerodynamic sizes of particles, based on their velocity in the measuring volume. More particularly, the air stream is accelerated as it leaves the coaxial nozzle assembly via exits 102 and 104. Thus, the air undergoes acceleration as it travels through measuring volume 36. The particles also are accelerated, but at a rate that lags the acceleration of the air. The extent of this lag, or relaxation time, varies with a particle's mass, size and shape. The aerodynamic sizes of particles vary linearly with particle relaxation times. When particle density is known, the measured aerodynamic size can be used to estimate particle mass. In lieu of the nozzle assembly, obstructions or curvature in a flow path can be used to selectively alter the fluid velocity in the region of the measuring volume, either by accelerating or decelerating the flow.

Figure 12:
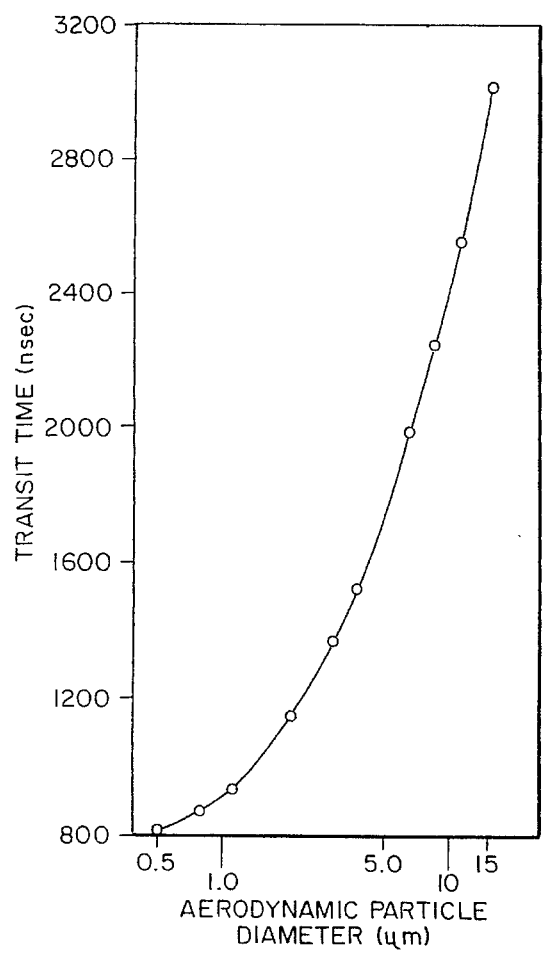
FIG. 12 is a chart plotting particle transit time with respect to aerodynamic particle diameter.

In theory, there is a precise mathematical relationship of aerodynamic size and velocity. However, given numerous (albeit small) variations in system configurations, it is highly preferred to calibrate system 16, based on a series of tests, each involving single spheres of a known, uniform size. Based on these tests, a mathematical function is empirically determined for relating time-of-flight measurements to aerodynamic particle sizes. This function is stored in the memory of processor 162, enabling the display of particle aerodynamic size information, based on the time/velocity information obtained. FIG. 12 is an example of a calibration curve, stored as a function in the processor.

Figure 13:
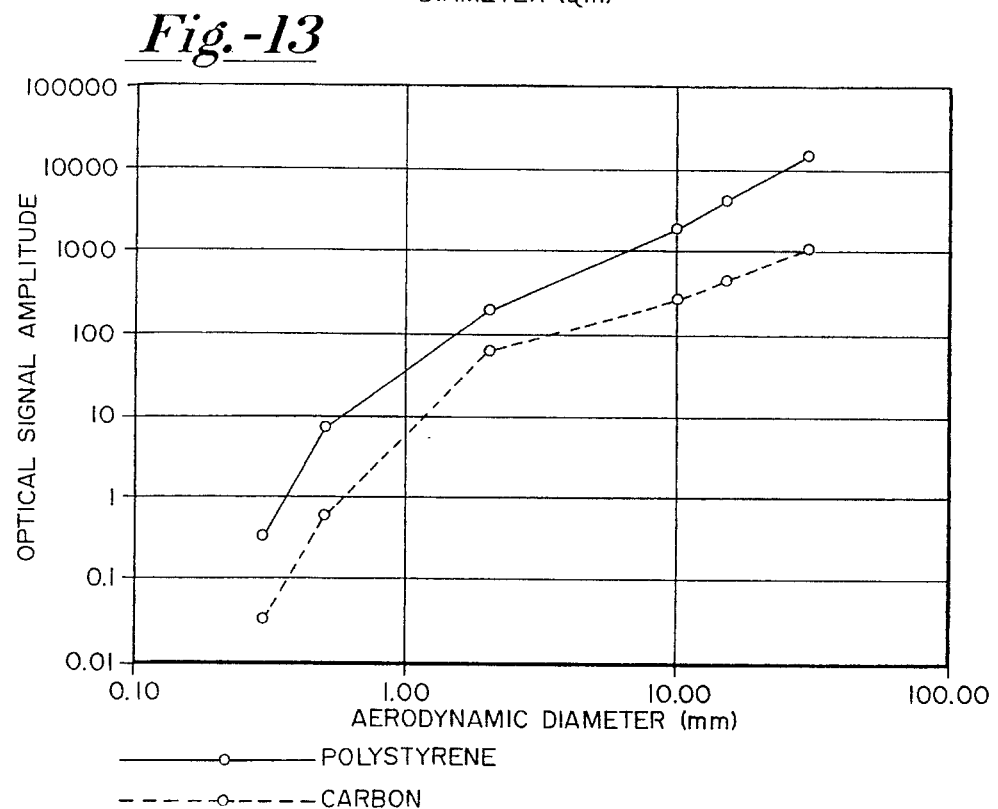
FIG. 13 is a chart plotting relative signal amplitudes with respect to particle aerodynamic diameters for two different materials.

As noted above, values can be obtained for a particle's aerodynamic size based on velocity, and optical size based on the amplitude of scattered (or extinguished) light. To this end, further calibration functions are stored in the memory of processor 162. FIG. 13 is a chart illustrating scattered light amplitude (proportional to optical size) as a function of the aerodynamic particle size for two materials: polystyrene and coal dust. Other materials likewise have unique functions of optical size relative to aerodynamic size. This information can be used to empirically determine the composition of particles, based on determining their aerodynamic and optical sizes. Alternatively, the dual size measurements can be employed to detect presence of particular particles (e.g. coal dust) within a background of other particles such as water droplets or soil dust.

Figure 14:
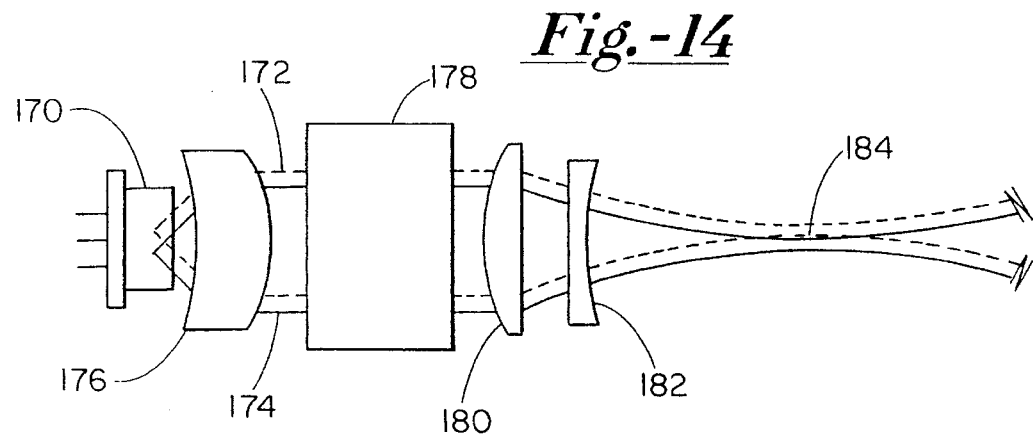
FIG. 14 is a diagrammatic view of a two element laser for beam generation in an alternative embodiment system.

FIG. 14 illustrates an alternative approach to generating the radiant energy to form the measuring volume. More particularly, a two-element laser source 170 generates two closely spaced beams 172 and 174 that diverge to a collimating lens 176. The collimated beams are directed through beam-shaping optics 178 that can include anamorphic prisms as well as cylindrical lenses. Emerging from the beam shaping optics, beams 172 and 174 are directed through a cylindrical telescope including cylindrical lenses 180 and 182, to bring both beams to a focus at a measuring volume 184 where the beams also peripherally overlap in the manner discussed above.

Figure 15:
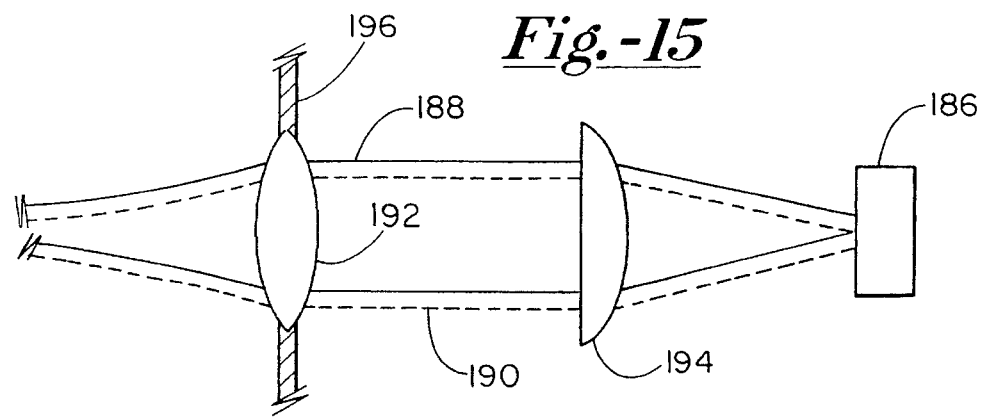
FIG. 15 is a partial view of a further embodiment system illustrating alternative light collection features.
Figure 16:
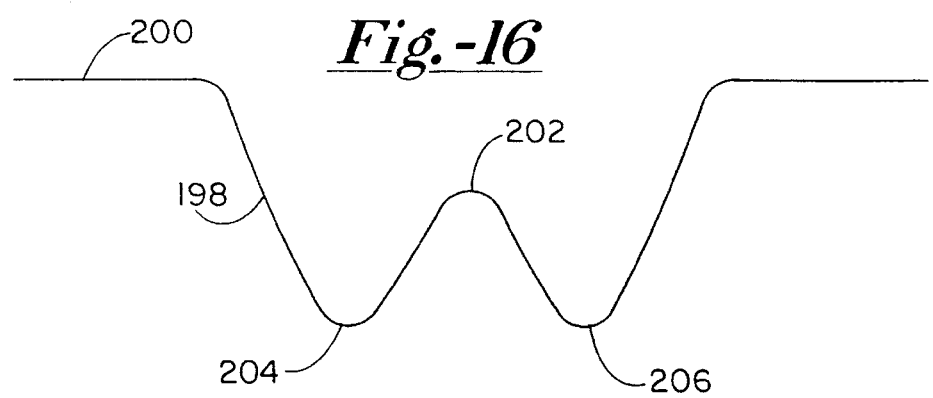
FIG. 16 shows a time-dependent amplitude profile generated by the system of FIG. 15.

FIG. 15 illustrates an alternative embodiment light collection means in which a photodetector 186 receives beams 188 and 190 directly as they emerge from the measuring volume. Spherical lenses 192 and 194, one of which is mounted in sealed fashion within a chamber wall 196, collect the emerging light and direct it to photodetector 186. This system relies on light extinction as a particle passes through the measuring volume. Accordingly, the photodetector output is a time-dependent voltage profile 198 which is the inverse of profile 106. As seen in FIG. 16 the background voltage 200 is the highest voltage level, with an intermediate level 202 positioned between the two minimum values of peaks 204 and 206. Signal processing is essentially the same, with time/velocity readings being accepted so long as profile 198 remains less than the threshold voltage.

Figure 17:
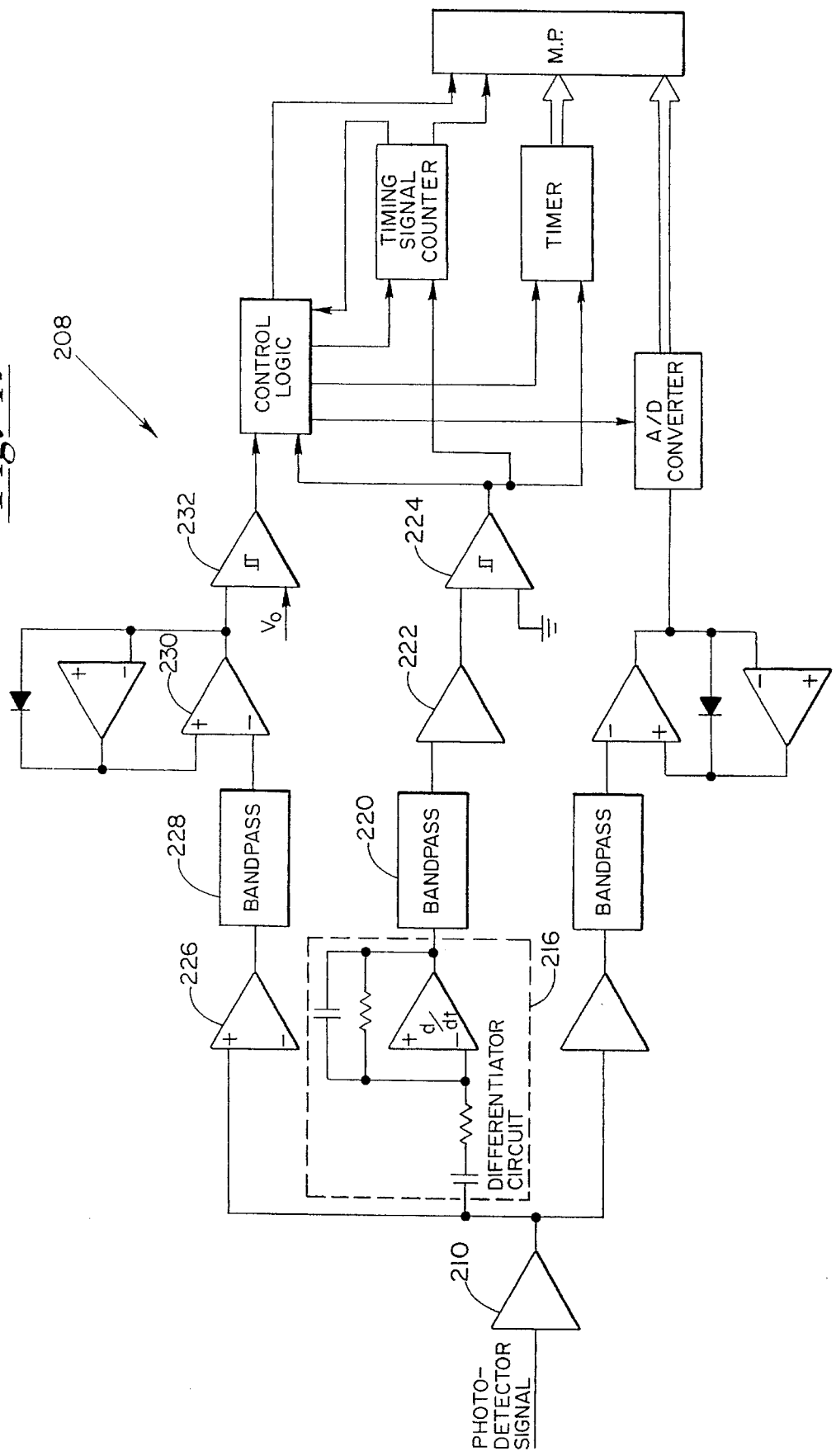
FIG. 17 is a partial view of a further embodiment system illustrating alternative signal processing circuitry.

FIG. 17 illustrates an alternative embodiment signal processing circuit 208 for employing differentiation in lieu of signal subtraction when deriving the timing signal. To obtain the timing signal, the output of a photodetector preamplifier 210 is provided to an analog differentiator and low-pass filter circuit 216. The differentiated signal is provided through a band-pass filter 220 to a clipping amplifier 222, the output of which is provided to a timing comparator 224.

The photodetector output is provided to an amplifier 226, then filtered at 228 at approximately one-half the band width of signals corresponding to the fastest expected particles of interest. This effectively removes the central minimum between peaks for a signal that remains continuously above the comparator threshold when a particle of sufficient size is within the measuring volume. Voltage profiles corresponding to slower particles retain more of the central minimum. However, since slower signals usually involve larger particles and thus have larger amplitudes, such signals also stay above the comparator threshold. The output of 228 is provided to a clipping amplifier 230 with baseline clamping and then to a gate signal comparator 232.

The amplitude-determining circuitry is essentially the same as that in circuit 124. Also, the control logic and other elements of the digital circuitry remain essentially the same.

Thus in accordance with the present invention, there is provided a substantially improved approach to deriving velocity of single particles, for determining aerodynamic particle sizes based on velocities, and for determining particle composition or other traits based on combined optical size and aerodynamic size. The controlled intensity profile across the measuring volume leads to a similarly controlled time-dependent voltage profile with upstream and downstream peaks and a lower amplitude between the peaks. By appropriately selecting the intermediate amplitude with respect to the peaks, the time-dependent voltage profile is made particularly well suited for generating a suitable threshold and for providing a pair of unambiguous zero transitions to accurately time particle travel.

What is claimed is:

1. An apparatus for measuring velocities of discrete elements carried in a fluid stream, including:

means for generating radiant energy, and for directing the radiant energy in a path that intersects a fluid stream to form a measuring volume wherein the fluid stream comprises a fluid and discrete elements carried in the fluid;

means for controlling the intensity of the radiant energy to vary selectively in a flow measurement direction in the measuring volume, whereby the measuring volume includes a first region of intensity, a second region of intensity downstream of the first region, and a third region of intermediate intensity disposed between and contiguous with the first and second regions, and each of the first and second regions has an intensity level greater than that of the intermediate region;

a light receiving means for receiving at least a portion of the radiant energy emerging from the measuring volume, said receiving means including detecting means for generating an electrical signal responsive to received radiant energy, said electrical signal having a background level when no element is present in the measuring volume and having a continuous time-dependent profile corresponding to the passage of one of the discrete elements through the measuring volume, said time-dependent profile including first and second peaks corresponding respectively to element travel through the first and second regions and further including an intermediate profile segment between the peaks, having a level between the background level and the level of each peak, corresponding to element travel through the third region;

means for measuring a time of travel for the element from a selected first location in one of the regions to a selected second location in another one of the regions, based on a first time-dependent distance from the first location to the second location, and for generating an element velocity value based on the first time-dependent distance;

means for generating a threshold signal representing a predetermined minimum level of departure from the background level; and a monitoring means for monitoring the time-dependent profile with respect to the threshold signal and for validating said velocity value only if the threshold signal remains between the time-dependent profile and the background level over the entire span of a second time-dependent distance from the first peak to the second peak.

2. The apparatus of claim 1 wherein:

said light-receiving means collects light scattered by the element, and the levels of the first and second peaks and the intermediate profile segment are greater than the background level.

3. The apparatus of claim 2 wherein:

the receiving means includes collection optics having a focal location in the measuring volume, and a detector means positioned to receive scattered light gathered by the collection optics.

4. The apparatus of claim 1 wherein:

said time-dependent profile is generated based on light extinguished by said elements, with the levels of said peaks being less than the level of the intermediate profile segment and background level; and said receiving means includes a detecting means positioned to receive the radiant energy directly from the radiant energy generating means.

5. The apparatus of claim 1 wherein:

said selected first and second locations are centered at said first and second peaks, respectively, and the first and second time-dependent distances coincide.

6. The apparatus of claim 1 wherein:

said radiant energy includes first and second beams, each beam having a substantially Gaussian intensity profile, said beams peripherally overlapping one another at least in the measuring volume to form said intermediate region.

7. The apparatus of claim 6 wherein:

said fluid stream, at least at the measuring volume, moves in a fluid flow direction; the fluid flow direction and the flow measurement direction coincide; and the beams are parallel to each other, and perpendicular to the fluid flow direction.

8. The apparatus of claim 6 wherein:

each of the beams is selectively shaped to have an elliptical profile having a major axis and a minor axis, wherein each major axis is at least ten times as long as its associated minor axis.

9. The apparatus of claim 6 wherein:

the beams are brought to a focus within the measuring volume.

10. The apparatus of claim 6 wherein:

said means for generating radiant energy includes a laser source for generating a single laser beam, and beam-splitting optics for separating the single beam into said first and second beams.

11. The apparatus of claim 10 wherein:

the means for generating radiant energy further includes a polarization means, whereby the first and second beams are orthogonally polarized.

12. The apparatus of claim 6 wherein:

said first and second beams of the radiant energy have substantially the same total intensity and substantially the same intensity profile.

13. The apparatus of claim 1 further including:

a means for delaying the time-dependent profile by a predetermined amount to generate a first time-delayed profile, and means for summing the time-dependent and time-delayed profiles to generate a summed signal.

14. The apparatus of claim 13 wherein:

said monitoring means includes a comparator means having said threshold signal and said summed signal as inputs, and generating a first digital logic output so long as the summed signal exceeds the threshold signal, and generating a second digital output whenever the threshold signal exceeds the summed signal.

15. The apparatus of claim 14 wherein:

said predetermined amount is approximately one-half of the expected minimum peak-to-peak time for said time-dependent profile.

16. The apparatus of claim 1 wherein:

said means for measuring a time of travel includes a pulse counter, a triggering means for initiating the pulse counter responsive to the element reaching said selected first location, and means for halting the counter responsive to the element reaching said selected second location.

17. The apparatus of claim 1 wherein:

said means for measuring a time of travel includes means for delaying the time-dependent profile by a predetermined amount to generate a time-delayed profile, means for subtracting the time-delayed profile from the time-dependent profile to generate a difference signal, and means for detecting negative-going zero crossings of the difference signal.

18. The apparatus of claim 17 wherein:

said selected first and second locations are substantially centered at said first and second peaks, respectively, and said predetermined amount is approximately one-half of the expected minimum peak-to-peak time for said time-dependent profile.

19. The apparatus of claim 16 wherein:

said triggering means includes means for differentiating the time-dependent profile to generate a differential signal, and means for detecting negative-going zero crossings of the differential signal.

20. The apparatus of claim 1 further including:

means for delaying the time-dependent profile by a first predetermined amount to generate a first time-delayed profile, means for subtracting the first time-delayed profile from the time-dependent profile to generate a difference signal having at least one zero crossing, and means for delaying the time-dependent profile by a second predetermined amount to generate a second time-delayed profile, said second predetermined amount being selected such that the zero crossing substantially coincides with one of the peaks of the second time-delayed profile.

21. The apparatus of claim 20 wherein:

said predetermined amount is equal to about one-half of an expected minimum amount for said second time-dependent distance.

22. The apparatus of claim 1 further including:

a means for generating the fluid stream and for altering the velocity of the fluid stream in the region of the measuring volume.

23. The apparatus of claim 22 wherein:

said means for generating the fluid stream and for altering the velocity of the fluid stream include a nozzle, a pump means for drawing the fluid through an exit of the nozzle immediately upstream of the measuring volume and for accelerating the fluid as it traverses the measuring volume, a filtering means for providing a filtered fluid substantially free of the elements, and a means for providing the filtered fluid in a substantially annular sheath flow around the nozzle, thereby to substantially confine the elements to a central region of the fluid stream.

24. The apparatus of claim 22 further including:

a means for determining an aerodynamic size of the element, based on said element velocity value.

25. The apparatus of claim 24 further including:

a means for determining an optical size of the element, based on a peak amplitude of the time-dependent profile.

26. The apparatus of claim 25 further including:

a means for determining a trait of the element, based on the aerodynamic size and the optical size.

27. A process for measuring velocities of discrete elements carried by a fluid stream, including:

directing radiant energy along a path that intersects a fluid stream to define a measuring volume within the fluid stream;

selectively controlling the intensity of the radiant energy to form, in the measuring volume and along a measurement direction, a first high intensity region, a second high intensity region downstream of the first region, and a third intensity region between and contiguous with the first and second regions, each of the first and second regions having a higher intensity than the third region;

generating an electrical signal responsive to radiant energy received from the measuring volume, with the electrical signal including a background level when no discrete element is present in the measuring volume and a continuous time-dependent profile corresponding to said fluid stream carrying a discreet element through the measuring volume; said time-dependent profile, by virtue of said controlled intensity, including first and second peaks corresponding respectively to travel of the element through the first region and the second region, and further including an intermediate profile segment between the peaks having a level between the background level and the level of each peak and corresponding to element travel through the third region;

determining a time of travel for the element from a selected first location in one of the regions to a selected second location in another one of the regions based on a first time-dependent distance along the time-dependent profile from the first location to the second location, and generating an element velocity value based on the first time-dependent distance;

selecting a threshold level; and selectively either (i) validating the element velocity value based on determining that the threshold level is between the background level and the level of the time-dependent profile, along the entire span of a second time-dependent distance from the first peak to the second peak; or (ii) rejecting the element velocity value as invalid, responsive to determining that the threshold level is not between the background level and the time-dependent profile level over the entire second time-dependent distance.

28. The process of claim 27 wherein:

said step of generating an electrical signal includes detecting radiant energy scattered by the element.

29. The process of claim 27 wherein:

the step of generating an electrical signal includes sensing the extent to which the element extinguishes the radiant energy.

30. The process of claim 27 wherein:

the step of generating radiant energy includes generating first and second radiant energy beams, each beam having a substantially Gaussian intensity profile, and causing the first and second beams to peripherally overlap one another at least in the measuring volume.

31. The process of claim 30 wherein:

the step of generating radiant energy includes selectively shaping the first and second beams into elliptical profiles with respective major and minor axes, with each major axis being at least ten times as long as its associated minor axis.

32. The process of claim 30 wherein:

the step of generating radiant energy further includes splitting a single radiant energy beam into said first and second beams.

33. The process of claim 30 wherein:

the step of generating radiant energy further includes causing the first and second beams to become orthogonally polarized.

34. The process of claim 27 further including the step of:

selectively delaying the time-dependent profile to generate a time-delayed profile, and adding the time-delayed profile to the time-dependent profile to generate a summed signal, and either validating or rejecting the element velocity value based on comparing the threshold level and the summed signal.

35. The process of claim 27 including the further step of:

delaying the time-dependent profile by approximately one-half of the expected minimum peak-to-peak time of said time-dependent profile to generate a difference signal, and detecting consecutive negative-going crossings of the difference signal to determine said first time-dependent distance and said element velocity value.

36. The process of claim 27 further including:

determining an aerodynamic size of the element, based on the element velocity value.

37. The process of claim 36 including the further step of:

determining the optical size of the element, based on the amplitude of the time-dependent profile.

38. The process of claim 37 including the further step of:

determining a trait of the element based on the optical size and the aerodynamic size.

39. The process of claim 36 wherein:

the step of determining aerodynamic size includes locating the measuring volume at a region where the fluid is undergoing acceleration.

40. The process of claim 35 including the further step of:

counting said negative-going zero crossings during the time that said threshold level remains between the background level and the level of the time-dependent profile, and accepting the element velocity value as valid only if the resulting count of the negative-going zero crossings is equal to two.

* * * * *